US006514918B1

(12) United States Patent
Librizzi

(10) Patent No.: US 6,514,918 B1
(45) Date of Patent: Feb. 4, 2003

(54) VISCOUS, MILD, AND EFFECTIVE CLEANSING COMPOSITIONS

(75) Inventor: Joseph J. Librizzi, Neshanic, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 148 days.

(21) Appl. No.: 09/641,644

(22) Filed: Aug. 18, 2000

(51) Int. Cl.⁷ .............................. C11D 1/14; C11D 1/86; C11D 1/94; C11D 3/32; C11D 3/20
(52) U.S. Cl. .................. 510/124; 510/125; 510/127; 510/137; 510/138; 510/158; 510/159; 510/499; 510/501; 510/504; 424/70.21; 424/70.24; 424/70.27; 424/70.28; 424/70.31
(58) Field of Search ........................ 510/124, 125, 510/127, 137, 138, 158, 159, 501, 499, 504; 424/70.21, 70.24, 70.27, 70.28, 70.31

(56) References Cited

U.S. PATENT DOCUMENTS

| | | |
|---|---|---|
| 3,903,008 A | 9/1975 | Deweever et al. |
| 4,205,063 A | 5/1980 | Khalil et al. |
| 4,336,151 A | 6/1982 | Like et al. |
| 4,364,837 A | 12/1982 | Pader |
| 4,420,410 A | 12/1983 | Hüttinger |
| 4,452,732 A | 6/1984 | Bolich, Jr. |
| 4,472,291 A | 9/1984 | Rosano |
| 4,544,495 A | 10/1985 | Scholka |
| 4,552,685 A | 11/1985 | Kernstock et al. |
| 4,636,329 A | 1/1987 | Steuri |
| 4,671,894 A | 6/1987 | Lamb et al. |
| 4,898,725 A | 2/1990 | Hoeffkes et al. |
| 4,948,576 A | 8/1990 | Verdicchio et al. |
| 5,009,813 A | 4/1991 | Watanabe et al. |
| 5,049,377 A | 9/1991 | Lamb et al. |
| 5,059,414 A | 10/1991 | Dallal et al. |
| 5,077,040 A | 12/1991 | Bergmann et al. |
| 5,077,041 A | 12/1991 | Yamashina et al. |
| 5,089,257 A | 2/1992 | Schrader et al. |
| 5,106,613 A | 4/1992 | Hartnett et al. |
| 5,124,078 A | 6/1992 | Baust |
| 5,145,607 A | 9/1992 | Rich |
| 5,152,914 A | 10/1992 | Forster et al. |
| 5,160,730 A | 11/1992 | Dubief et al. |
| 5,180,584 A | 1/1993 | Sebag et al. |
| 5,186,929 A | 2/1993 | DeMarco et al. |
| 5,221,530 A | 6/1993 | Janchitraponvej et al. |
| 5,252,324 A | 10/1993 | Bires et al. |
| 5,275,761 A | 1/1994 | Bergmann |
| 5,290,482 A | 3/1994 | Marschner et al. |
| 5,302,322 A | 4/1994 | Birtwistle |
| 5,328,630 A | 7/1994 | Nozaki et al. |
| 5,348,736 A | 9/1994 | Patel et al. |
| 5,387,373 A | 2/1995 | Naik |
| 5,391,368 A | 2/1995 | Gerstein |
| 5,403,508 A | 4/1995 | Reng et al. |
| 5,417,965 A * | 5/1995 | Janchitraponvej et al. ....... 424/70.12 |
| 5,437,809 A | 8/1995 | Chaudhuri |
| 5,474,835 A | 12/1995 | McCarthy et al. |
| 5,543,074 A | 8/1996 | Hague et al. |
| 5,573,709 A | 11/1996 | Wells |
| 5,576,279 A * | 11/1996 | Pyles ........................ 510/122 |
| 5,656,258 A | 8/1997 | Cauwet et al. |
| 5,705,692 A | 1/1998 | Wang et al. |
| 5,712,241 A * | 1/1998 | Gorlin et al. ............... 510/426 |
| 5,714,446 A | 2/1998 | Bartz et al. |
| 4,731,201 A | 3/1998 | Robbins et al. |
| 4,741,855 A | 5/1998 | Grote et al. |
| 5,756,436 A | 5/1998 | Royce et al. |
| 5,757,436 A | 5/1998 | Royce et al. |
| 5,776,444 A | 7/1998 | Birtwistle et al. |
| 5,776,871 A | 7/1998 | Cothran et al. |
| 5,788,884 A | 8/1998 | Kuwata et al. |
| 5,792,737 A | 8/1998 | Grüning et al. |
| 5,804,207 A | 9/1998 | Dubief et al. |
| 5,830,438 A | 11/1998 | Dupuis |
| 5,843,875 A | 12/1998 | Wei et al. |
| 5,856,544 A | 1/1999 | Czech et al. |
| 5,876,705 A | 3/1999 | Uchiyama et al. |
| 5,883,058 A | 3/1999 | Wells et al. |
| 5,905,062 A | 5/1999 | Elliott et al. |
| 5,910,472 A | 6/1999 | Elliott et al. |
| 5,910,477 A | 6/1999 | Gordon |
| 5,919,749 A | 7/1999 | Sakamoto et al. |
| 5,942,478 A | 8/1999 | Lopes |
| 5,942,479 A | 8/1999 | Frankenbach et al. |
| 5,958,390 A | 9/1999 | Sanner et al. |
| 5,958,392 A | 9/1999 | Grollier et al. |
| 5,965,502 A | 10/1999 | Balzer |
| 5,976,517 A | 11/1999 | Dubief et al. |
| 5,977,038 A | 11/1999 | Birtwistle et al. |
| 5,985,254 A | 11/1999 | Hirano et al. |
| 5,990,059 A | 11/1999 | Finel et al. |
| 6,010,990 A | 1/2000 | Rousso et al. |
| 6,022,836 A | 2/2000 | Dubief et al. |
| 6,030,935 A * | 2/2000 | Drapier et al. ............... 510/417 |
| 6,056,945 A | 5/2000 | Cauwet-Martin et al. |
| 6,074,633 A | 6/2000 | Dubief et al. |
| 6,132,707 A | 10/2000 | Dubief et al. |
| 6,165,446 A | 12/2000 | Samain et al. |

FOREIGN PATENT DOCUMENTS

CA          2017672 C      11/1990

(List continued on next page.)

*Primary Examiner*—Gregory Delcotto
(74) *Attorney, Agent, or Firm*—Michele G. Mangini

(57) ABSTRACT

A cleansing composition, which is mild to the skin and eyes is disclosed. The composition includes a compound of formula I

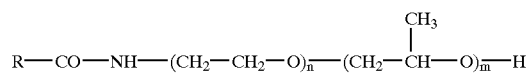

$$R-CO-NH-(CH_2-CH_2-O)_{\overline{n}}-(CH_2-CH-O)_{\overline{m}}-H$$
with a $CH_3$ branch on the CH carbon (I)

wherein: R=$C_6$ to $C_{30}$ Fatty Acid, n=0 to 20, m=0 to 40, and n+m=2 to 60; and at least one anionic surfactant. The composition may further include nonionic, amphoteric, betaine, and cationic surfactants. The compositions are useful as shampoos, washes, baths, gels, lotions, creams, and the like.

23 Claims, No Drawings

FOREIGN PATENT DOCUMENTS

| | | |
|---|---|---|
| CA | 2028226 A1 | 4/1991 |
| CA | 2031382 C | 6/1991 |
| CA | 2075117 C | 2/1993 |
| CA | 2139495 A1 | 1/1994 |
| CA | 2141328 A1 | 2/1994 |
| CA | 2180942 A1 | 8/1995 |
| CA | 2145474 A1 | 10/1995 |
| CA | 2215751 A1 | 10/1996 |
| CA | 2218683 A1 | 10/1996 |
| CA | 2234851 A1 | 4/1997 |
| CA | 2250384 A1 | 10/1997 |
| CA | 2250385 A1 | 10/1997 |
| CA | 2250389 A1 | 10/1997 |
| CA | 2257188 A1 | 12/1997 |
| CA | 2259658 A1 | 1/1998 |
| CA | 2259661 A1 | 1/1998 |
| CA | 2261755 A1 | 2/1998 |
| CA | 2265652 A1 | 4/1998 |
| CA | 2269762 A1 | 5/1998 |
| CA | 2269822 A1 | 5/1998 |
| CA | 2271078 A1 | 5/1998 |
| CA | 2274849 A1 | 7/1998 |
| CA | 2120492 C | 12/1999 |
| CA | 2278409 A1 | 1/2000 |
| EP | 0014479 B1 | 8/1980 |
| EP | 0034190 B1 | 8/1981 |
| EP | 0045720 B1 | 2/1982 |
| EP | 0047714 B1 | 3/1982 |
| EP | 0080976 B1 | 6/1983 |
| EP | 0080976 A1 | 6/1983 |
| EP | 0127580 A2 | 12/1984 |
| EP | 0181773 B2 | 5/1986 |
| EP | 0231997 B1 | 8/1987 |
| EP | 0240350 B1 | 10/1987 |
| EP | 0257807 B1 | 3/1988 |
| EP | 322 741 B1 | 7/1989 |
| EP | 0357351 B1 | 3/1990 |
| EP | 0370764 B1 | 5/1990 |
| EP | 0381318 B1 | 8/1990 |
| EP | 0400976 B1 | 12/1990 |
| EP | 0412705 B1 | 2/1991 |
| EP | 0412706 B1 | 2/1991 |
| EP | 0412710 B1 | 2/1991 |
| EP | 0413417 B1 | 2/1991 |
| EP | 0437114 B1 | 7/1991 |
| EP | 0460683 A2 | 12/1991 |
| EP | 0490582 A1 | 6/1992 |
| EP | 0492657 B1 | 7/1992 |
| EP | 0514934 B1 | 11/1992 |
| EP | 0514934 A1 | 11/1992 |
| EP | 0529883 B1 | 3/1993 |
| EP | 0530974 B1 | 3/1993 |
| EP | 0551749 B1 | 7/1993 |
| EP | 0357351 B1 | 10/1993 |
| EP | 0487211 B1 | 10/1994 |
| EP | 0658100 B1 | 6/1995 |
| EP | 0659405 B1 | 6/1995 |
| EP | 0662315 B1 | 7/1995 |
| EP | 0674898 A2 | 10/1995 |
| EP | 0511652 B1 | 11/1995 |
| EP | 0687459 B1 | 12/1995 |
| EP | 0560896 B1 | 3/1996 |
| EP | 0687459 B1 | 8/1996 |
| EP | 0461593 B1 | 9/1996 |
| EP | 0741558 B1 | 11/1996 |
| EP | 0756860 A1 | 2/1997 |
| EP | 0758545 A1 | 2/1997 |
| EP | 0773015 A2 | 5/1997 |
| EP | 0786250 A1 | 7/1997 |
| EP | 0796614 A1 | 9/1997 |
| EP | 0796615 A1 | 9/1997 |
| EP | 0821934 A1 | 2/1998 |
| EP | 0823249 B1 | 2/1998 |
| EP | 0648105 B1 | 6/1998 |
| EP | 0855178 A2 | 7/1998 |
| EP | 0862908 A2 | 9/1998 |
| EP | 0787485 B1 | 11/1998 |
| EP | 0893117 A2 | 1/1999 |
| EP | 0913390 A2 | 5/1999 |
| GB | 2027045 B | 2/1980 |
| GB | 2136689 B | 2/1980 |
| GB | 2039938 B | 8/1980 |
| GB | 2063671 B | 6/1981 |
| GB | 2088209 B | 6/1982 |
| GB | 2104091 B | 3/1983 |
| GB | 2114580 B | 8/1983 |
| GB | 2131821 B | 6/1984 |
| GB | 2135332 B | 8/1984 |
| GB | 2134784 B | 8/1986 |
| WO | WO92/10990 A1 | 7/1992 |
| WO | WO94/06403 A1 | 3/1994 |
| WO | WO94/18934 A1 | 9/1994 |
| WO | WO95/23579 A2 | 9/1995 |
| WO | WO97/09031 A1 | 3/1997 |
| WO | WO97/12595 A1 | 4/1997 |
| WO | WO97/14396 A1 | 4/1997 |
| WO | WO97/14400 A1 | 4/1997 |
| WO | WO97/26860 A1 | 7/1997 |
| WO | WO97/35544 A1 | 10/1997 |
| WO | WO98/05296 A1 | 2/1998 |
| WO | WO98/13011 A1 | 4/1998 |
| WO | WO98/18435 A2 | 5/1998 |
| WO | WO98/18443 A1 | 5/1998 |
| WO | WO98/19655 A1 | 5/1998 |
| WO | WO98/19656 A1 | 5/1998 |
| WO | WO99/07333 A1 | 2/1999 |
| WO | WO99/09947 A1 | 3/1999 |
| WO | WO99/13842 A1 | 3/1999 |
| WO | WO99/13843 A1 | 3/1999 |

* cited by examiner

VISCOUS, MILD, AND EFFECTIVE CLEANSING COMPOSITIONS

BACKGROUND OF THE INVENTION

1. Field of the Invention

The present invention relates to a cleansing composition, which is mild to the skin and eyes and possesses sufficient viscosity with appropriate cleansing and foaming performance.

2. Description of the Prior Art

Historically, many mild cleansing compositions suffer from poor foaming and cleansing performance. As used herein, the term "mild cleansing compositions" refer to compositions that, when instilled into human eyes at about a 10% dilution level, cause an ocular irritation that is less than or equivalent to the irritation caused by a similar addition of sterile water thereto. In many cases, the ocular stinging effect of a composition on the eye is concentration dependent. Therefore, one way to reduce ocular irritancy is to minimize the amount of the cleansing composition that gets into the eye via increasing the viscosity of the product. For example, the viscosity of a shampoo may be sufficiently increased in order to minimize the amount that may drip from the head into the eyes during its use. However, it can be difficult or costly to thicken shampoos.

One known method for thickening mild cleansing compositions is via the addition of a viscosity builder such as a salt, e.g. sodium chloride, to a cleansing composition. However, the use of sodium chloride at high levels negatively impacts eye irritation. Another method for thickening mild cleansing compositions is via the addition of polymeric thickeners such as hydroxyethyl cellulose to the composition. Unfortunately, many of the polymeric thickeners are incompatible with surfactant systems and therefore contribute to instability of the final product. Yet another popular method for thickening mild cleansing compositions is via the addition of a polyol alkoxy ester to the composition. In each of these approaches, the compound is added merely to build viscosity of the cleansing system, thereby adding cost while contributing little else to the performance of the system.

A better approach to the problem is to incorporate surfactants that both build viscosity and contribute to the foaming and cleansing performance of the surfactant system while maintaining low cost. One such class of surfactants that have been used extensively for this purpose includes the alkanolamides, such as the fatty acid diethanotamides. The use of ethoxylated diethanolamines as irritancy mitigators has been described in U.S. Pat. No. 4,336,151. In U.S. Pat. No. 4,205,063, the use of fatty acid diethanolamide has been described in low irritation shampoo formulas as a foam booster. Unfortunately, the use of diethanolamides in cosmetic preparations has recently come under scrutiny due to safety concerns regarding their possible carcinogenicity.

Therefore, there is a need for a cosmetic ingredient that is capable of viscosity building and foam boosting without compromising the mildness and safety properties of the overall cleansing composition.

SUMMARY OF THE INVENTION

It has been discovered that the aforementioned objective can be achieved by selecting specific compounds to increase the viscosity while building the foam of a cleansing composition. The present invention provides a cleansing composition including a compound of formula I

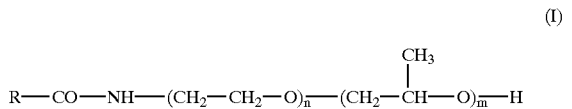

wherein: R=$C_6$ to $C_{30}$ Fatty Acid, n=0 to 20, m=0 to 40, and n+m=2 to 60; and at least one anionic surfactant; wherein the composition is mild.

DETAILED DESCRIPTION OF PREFERRED EMBODIMENTS

The cleansing composition of the present invention is comprised of, consists of, and/or consists essentially of, based upon the total weight of the composition, a) from about 0.01% to about 10.0%, e.g. from about 0.1% to about 7.0% and from about 0.5% to about 3.0% of the compound of Formula I. and b) from about 0.1% to about 20%, e.g. from about 0.5% to about 10% and from about 0.75% to about 5% of an anionic surfactant.

The compound of Formula I may be selected from ethoxylated fatty amides, propoxylated fatty amides, fatty amides that contain both ethoxylate and propoxylate groups, and mixtures thereof. Suitable compounds include, but are not limited to, polyethylene glycol ("PEG")-6 Cocamide, PEG-6 Lauramide, PEG-3 Cocamide, polypropylene glycol ("PPG")-2 Hydroxyethyl Cocamide, PPG-1 Hydroxyethyl Caprylamide, and PPG-3 Hydroxyethyl Linoleamide. The preferred compounds include PPG-2 Hydroxyethyl Cocamide, which is available from Uniqema under the tradename, "Promidium CO", PPG-1 Hydroxyethyl Caprylamide, which is available from Uniqema under the tradename, "Promidium CC", PPG-3 Hydroxyethyl Linoleamide, which is available from Uniqema under the tradename, "Promidium SY", and PEG-3 Cocamide, which is available from Heterene, Inc. under the tradename, "Hetoxamide CD-4."

Classes of anionic surfactants useful in this invention include the alkyl sulfates, alkyl ether sulfates, sulfosuccinates, isethionates, acyl amides, alkyl ether carboxylates and alkyl phosphates, wherein the alkyl group has from about 6 carbon atoms to about 30 carbon atoms, with about 10 to about 14 carbon atoms being preferred.

In addition to at least one anionic surfactant, the mild cleansing composition of the invention may optionally contain a secondary surfactant selected from nonionic, amphoteric, betaine, cationic, and mixtures thereof. The total amount of anionic surfactant and secondary surfactant (s) that are suitable for use in the composition of the present invention may range from, based upon the total weight of the total cleansing composition, from about 2.5% to about 50%, e.g. from about 5% to about 40% and from about 8% to about 25%.

Types of nonionic surfactants that are suitable for use in this invention include the fatty alcohol acid or amide ethoxylates, monoglyceride ethoxylates, sorbitan ester ethoxylates and alkyl polyglycosides. These nonionic surfactants can be employed in composition of the present invention in an amount, based upon the total weight of the composition, from about 0.0% to about 30%, e.g. from about 0.1% to about 20% and from about 0.1% to about 15%.

Classes of amphoteric surfactants that are suitable for use in this invention include alkylimino-diproprionates, alkylamphoglycinates (mono or di), alkylamphoproprionates (mono or di), alkylamphoacetates (mono or di), N-alkyl β-aminoproprionic acids, alkylpolyamino carboxylates, and phosphorylated imidazolines. These amphoteric surfactants can be employed in composition of the present invention in an amount, based upon the total weight of the composition, from about 0.1% to about 20%, e.g. from about 0.1% to about 15% and from about 0.1% to about 10%.

Types of betaines that are suitable for use in this invention include alkyl betaines, alkylamido betaines, alkyl sultaines and alkylamido sultaines, wherein the alkyl group has from about 6 carbon atoms to about 30 carbon atoms, with about 10 to about 14 carbon atoms being preferred. These betaine surfactants can be employed in the cleansing composition of the present invention in an amount, based upon the total weight of the cleansing composition, from about 0.1% to about 15%, e.g. from about 0.1% to about 10% and from about 0.1% to about 8%.

Classes of cationic surfactants that are suitable for use in this invention include alkyl quaternaries (mono, di, or tri), benzyl quaternaries, ester quaternaries, ethoxylated quaternaries, alkyl amines, and mixtures thereof, wherein the alkyl group has from about 6 carbon atoms to about 30 carbon atoms, with about 8 to about 22 carbon atoms being preferred. These cationic surfactants can be employed in composition of the present invention in an amount, based upon the total weight of the composition, from about 0.01% to about 20%, preferably from about 0.05% to about 15% and more preferably from about 0.1% to about 10%.

Optionally, the mild cleansing compositions of this invention may also contain, based upon the total weight of the mild cleansing composition, from about 0.01 percent to about 1.0 percent, preferably from about 0.01 percent to about 0.5 percent, and more preferably from about 0.01 to about 0.2 percent of at least one conditioning agent. Examples of suitable cationic conditioning agents nonexclusively include cationic cellulose derivatives; cationic guar derivatives; and diallyldimethylammonium chloride. Other suitable conditioning agents include those disclosed in U.S. Pat. No. 5,876,705, which is incorporated herein by reference. Surfactant soluble non-volatile silicone conditioning agents are also useful.

The cationic cellulose derivative may be a polymeric quaternary ammonium salt derived from the reaction of hydroxyethyl cellulose with a trimethylammonium substituted epoxide. The material known as Polyquaternium-10, commercially available from Amerchol Corporation of Edison, N.J. as "Polymer JR-400," is especially useful in this regard.

The cationic guar derivative may be a guar hydroxypropyltrimonium chloride, available commercially from Rhodia of Cranbury, N.J. under the tradename, "Jaguar C-17."

Other useful cationic conditioning polymers are those derived from the monomer diallyldimethylammonium chloride. The homopolymer of this monomer is Polyquaternium-6, which is available commercially form Allied Colloids of Suffolk, Va. under the tradename, "Salcare SC30." The copolymer of diallyldimethylammonium chloride with acrylamide is known as Polyquaternium-7, and is also available from Allied Colloids under the tradename "Salcare SC10."

The mild cleansing compositions of the present invention may also include one or more optional ingredients nonexclusively including a pearlescent or opacifying agent, a thickening agent, secondary conditioners, humectants, chelating agents, and additives which enhance their appearance, feel and fragrance, such as colorants, fragrances, preservatives, pH adjusting agents, and the like.

The pH of the mild cleansing compositions of this invention is preferably maintained in the range of from about 5 to about 7.5, and more preferably from about 5.5 to about 7.0.

Commercially available pearlescent or opacifying agents which are capable of suspending water insoluble additives such as silicones and/or which tend to indicate to consumers that the resultant product is a conditioning shampoo are suitable for use in this invention. The pearlescent or opacifying agent may be present in an amount, based upon the total weight of the composition, of from about 1 percent to about 10 percent, preferably from about 1.5 percent to about 7 percent, and more preferably, from about 2 percent to about 5 percent. Examples of suitable pearlescent or opacifying agents include, but are not limited to mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula: HO—(JO)$_a$—H, wherein J is an alkylene group having from about 2 to about 3 carbon atoms; and a is 2 or 3;fatty alcohols containing from about 16 to about 22 carbon atoms; fatty esters of the formula: KCOOCH$_2$L, wherein K and L independently contain from about 15 to about 21 carbon atoms; inorganic solids insoluble in the shampoo composition, and mixtures thereof The pearlescent or opacifying agent may be introduced to the mild cleansing composition as a pre-formed, stabilized aqueous dispersion, such as that commercially available from Henkel Corporation of Hoboken, N.J. under the tradename, "Euperlan PK-3000." This material is a combination of glycol distearate (the diester of ethylene glycol and stearic acid), Laureth-4 (CH$_3$(CH$_2$)$_{10}$CH$_2$(OCH$_2$CH$_2$)$_4$OH) and cocamidopropyl betaine and preferably is in a weight percent ratio of from about 25 to about 30: about 3 to about 15: about 20 to about 25, respectively.

Commercially available thickening agents, which are capable of imparting the appropriate viscosity to the mild cleansing compositions are suitable for use in this invention. If used, the thickener should be present in the shampoo compositions in an amount sufficient to raise the Brookfield viscosity of the composition to a value of between about 500 to about 10,000 centipoise. Examples of suitable thickening agents nonexclusively include: mono or diesters of 1) polyethylene glycol of formula: HO—(CH$_2$CH$_2$O)$_z$H, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

Commercially available secondary conditioners, such as volatile silicones, which impart additional attributes, such as gloss to the hair are suitable for use in this invention. Preferably, the volatile silicone conditioning agent has an atmospheric pressure boiling point less than about 220° C. The volatile silicone conditioner may be present in an amount of from about 0 percent to about 3 percent, preferably from about 0.25 percent to about 2.5 percent, and more preferably from about 0.5 percent to about 1.0 percent, based on the overall weight of the composition. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Coming Corporation of Midland, Mich. under the tradename, "DC-345" and mixtures thereof, and preferably include cyclomethicone fluids.

Commercially available humectants, which are capable of providing moisturization and conditioning properties to the mild cleansing composition, are suitable for use in the present invention. The humectant may be present in an amount of from about 0 percent to about 10 percent, preferably from about 0.5 percent to about 5 percent, and more preferably from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, and mixtures thereof; 2) polyalkylene glycol of the formula: $HO\text{—}(R"O)_b\text{—}H$, wherein R" is an alkylene group having from about 2 to about 3 carbon atoms and b is an integer of from about 2 to about 10; 3) polyethylene glycol ether of methyl glucose of formula $CH_3\text{–}C_6H_{10}O_5\text{—}(OCH_2CH_2)_c\text{—}OH$, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 100XL" and is present in an amount, based upon the total weight of the composition, from about 0 to about 0.5 percent, and preferably from about 0.05 percent to about 0.25 percent.

Suitable preservatives include Quaternium-15, available commercially as "Dowicil 200" from the Dow Chemical Corporation of Midland, Mich., and are present in the composition in an amount, based upon the total weight of the composition, from about 0 to about 0.2 percent, and preferably from about 0.05 percent to about 0.10 percent.

The above described mild cleansing composition may be prepared by combining the desired components in a suitable container and mixing them under ambient conditions in any conventional mixing means well known in the art, such as a mechanically stirred propeller, paddle, and the like. Although the order of mixing is not critical, it is preferable to pre-blend certain components, such as the fragrance and the nonionic surfactant before adding such components into the main mixture.

The compositions of the present invention are preferably used in personal care products such as shampoos, washes, baths, gels, lotions, creams, and the like.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

The following tests were used in the Examples:

1. Foam Generation: 1 g of a cleansing composition sample was added to a tray containing 5 liters of tap water, then gently mixed until homogenous without generating any foam. A Model AJMP14 Jiffy Mixer mechanical mixer available from U.S. Best, Inc. with an attached propeller blade was then set at a level in the tray such that the propeller blade was halfway immersed in the mixture. The mixer was then activated at a speed of 2000 RPM for 30 seconds to generate foam. Foam data was collected via photography using a Polaroid MP4+ camera at 30 seconds after the mixing was ceased. The area of foam in the tray was calculated and reported as % area of foam in tray.

2. Ocular Irritancy Test: Using a double-blinded, randomized, two (2) cell study test design, one (1) drop of a sample (e.g. a 10% dilution of a cleansing composition in water) at a temperature of about 38° C. was instilled into a subject's eye. A new sterile disposable eyedropper was used for each sample and disposed of after being used on only one individual's eye. All instillations were performed either by an investigator or by a trained technician.

Within 30 seconds, or as closely as possible following instillation, the subject was asked to grade the perceived stinging sensation to the eye utilizing the following criteria:

Sting
0=Within normal limits
1=Mild, very slight
2=Moderate
3=Severe

After 15 minutes and 60 minutes post-instillation, the subject was again asked to grade the perceived stinging sensation to the eye. The data was collected from a balanced, complete block experiment then statistically analyzed.

Examples 1–8

Preparation of Cleansing Compositions

The cleansing compositions of Examples 1 through 8 were prepared according to the materials and amounts listed in Table 1.

TABLE 1

| INCI Name | 1 | 2 | 3 | 4 | 5 | 6 | 7 | 8 |
|---|---|---|---|---|---|---|---|---|
| Disodium Lauroamphodiacetate | 0.6 | 0.6 | 0.6 | 0.6 | 0.6 | 0.6 | 0.6 | 0.6 |
| Sodium Trideceth Sulfate | 3.0 | 3.0 | 3.0 | 3.0 | 3.0 | 3.0 | 3.0 | 3.0 |
| PEG-6 Cocamide | — | 1.0 | — | — | — | — | — | — |
| PEG-6 Lauramide | — | — | 1.0 | — | — | — | — | — |
| PEG-3 Cocamide | — | — | — | 1.0 | — | — | — | — |
| Cocamide MIPA | — | — | — | — | 1.0 | — | — | — |
| Cocamide MEA | — | — | — | — | — | 1.0 | — | — |
| Cocamide DEA | — | — | — | — | — | — | 1.0 | — |
| PPG-2 Hydroxyethyl Cocamide | — | — | — | — | — | — | — | 1.0 |
| Quaternium-22 | 0.37 | 0.37 | 0.37 | 0.37 | 0.37 | 0.37 | 0.37 | 0.37 |
| Glycerin | 1.9 | 1.9 | 1.9 | 1.9 | 1.9 | 1.9 | 1.9 | 1.9 |

TABLE 1-continued

| INCI Name | 1 | 2 | 3 | 4 | 5 | 6 | 7 | 8 |
|---|---|---|---|---|---|---|---|---|
| PEG-120 Methyl Glucose Dioleate | 1.0 | 1.0 | 1.0 | 1.0 | 1.0 | 1.0 | 1.0 | 1.0 |
| POE 80 Sorbitan Monolaurate | 3.3 | 3.3 | 3.3 | 3.3 | 3.3 | 3.3 | 3.3 | 3.3 |
| Sodium Laureth-13 Carboxylate | 0.23 | 0.23 | 0.23 | 0.23 | 0.23 | 0.23 | 0.23 | 0.23 |
| Polyquaternium 10 | 0.14 | 0.14 | 0.14 | 0.14 | 0.14 | 0.14 | 0.14 | 0.14 |
| Cocamidopropyl Betaine | 2.8 | 2.8 | 2.8 | 2.8 | 2.8 | 2.8 | 2.8 | 2.8 |
| Tetrasodium EDTA | 0.10 | 0.10 | 0.10 | 0.10 | 0.10 | 0.10 | 0.10 | 0.10 |
| Quaternium 15 | 0.05 | 0.05 | 0.05 | 0.05 | 0.05 | 0.05 | 0.05 | 0.05 |
| Citric Acid, USP | 0.10 | 0.10 | 0.10 | 0.10 | 0.10 | 0.10 | 0.10 | 0.10 |
| Water | 86.43 | 85.43 | 85.43 | 85.43 | 85.43 | 85.43 | 85.43 | 85.43 |

The compositions of Examples 1 were prepared as follows:

Component amounts in this procedure are given in terms of parts by weight of active to prepare 100 parts of the cleansing composition. Water (50.0 parts) was heated to a temperature of about 50° C. to 55° C. with agitation. To the water was added 1.0 part of Polyquaternium-10 with agitation until the solution was homogenous. After 1.0 part of Quaternium-22 was added thereto with agitation until the solution was homogenous, 1.0 part of PEG-120 Methyl Glucose Dioleate was then added with agitation until all of the PEG-120 Methyl Glucose Dioleate dissolved. After 0.23 parts of Sodium Laureth-13 Carboxylate were added thereto with agitation until the solution was homogenous, cooling was commenced. The following components were then added sequentially thereto: 2.8 parts Cocamidopropyl Betaine, 0.6 parts Disodium Lauroamphodiacetate, 1.0 part Ethoxylated and/or Propoxylated Fatty Amide, 3.0 parts Sodium Trideceth Sulfate, and 3.3 parts of POE-80 Sorbitan Monolaurate.

After this mixture had cooled to a temperature not greater than 40° C., the following components were added sequentially thereto: 0.10 parts Tetrasodium EDTA, 0.05 parts Quaternium-15, and 1.9 parts Glycerin. After this solution mixture had cooled to room temperature (approximately 25° C.), the pH of the resulting solution was then adjusted with a 20% citric acid solution until a final pH of 6.0 to 6.6 was obtained. The batch weight of the solution was then adjusted with water in order to achieve a total formulation of 100 parts. Table 2 lists the final batch viscosity of each Example as measured by a Brookfield DV-I+Viscometer using the indicated spindle and speed.

TABLE 2

| | Final Viscosity (cps) | Brookfield Spindle @ Speed |
|---|---|---|
| Example 1 | 92.4 | #1 @ 6 RPM |
| Example 2 | 208 | #2 @ 30 RPM |
| Example 3 | 256 | #2 @ 30 RPM |
| Example 4 | 652 | #2 @ 30 RPM |
| Example 5 | 2970 | #2 @ 6 RPM |
| Example 6 | 2390 | #2 @ 6 RPM |
| Example 7 | 1735 | #2 @ 6 RPM |
| Example 8 | 1252 | #2 @ 30 RPM |

The viscosity of the examples was considered acceptable if it was at least twice the viscosity of Example 1. The data above demonstrate that PEG-6 Cocamide, PEG-6 Lauramide, PEG-3 Cocamide, Cocamide MIPA, Cocamide MEA, Cocamide DEA, and PPG-2 Hydroxyethyl Cocamide were effective at increasing the viscosity of a mild cleansing composition.

Examples 9–16
Foam Performance Evaluation

Foam performance evaluation was then accomplished for each of the cleansing compositions of Examples 1–8. Results of the Foam Tray Test are reported in Table 3 below.

TABLE 3

Foam Performance Evaluation

| | Foam Quantity @ 30 Seconds (%) |
|---|---|
| Example 1 | 3.00 |
| Example 2 | 49.0 |
| Example 3 | 68.5 |
| Example 4 | 63.8 |
| Example 5 | 12.0 |
| Example 6 | 19.5 |
| Example 7 | 13.5 |
| Example 8 | 13.0 |

Foaming of the Examples was considered acceptable if it was at least twice the amount of foam of Example 1. These Examples show that PEG-6 Cocamide, PEG-6 Lauramide, PEG-3 Cocamide, Cocamide MIPA, Cocamide MEA, Cocamide DEA, and PPG-2 Hydroxyethyl Cocamide are effective at increasing foam generation in mild cleansing compositions.

Examples 17–24
Ocular Irritancy Test

The samples of Examples 1–8 were tested for ocular irritancy. The results are reported in Table 4 in terms of the percentage of subjects who found the respective sample to be stinging to their eyes.

TABLE 4

| | Human Ocular Sting (EXAMPLE) | Statistical Significance |
|---|---|---|
| Example 1 | 0% | NS |
| Example 2 | 7% | NS |
| Example 3 | 7% | NS |
| Example 4 | 3% | NS |
| Example 5 | 40% | * |
| Example 6 | 37% | * |
| Example 7 | 13% | NS |
| Example 8 | 13% | NS |

NS = Example not statistically different than Control.
* = Example is statistically different than Control.

A sample was considered to have low ocular irritancy if less than 20% of the people tested found the sample to sting their eyes.

This Example shows that PEG-6 Cocamide, PEG-6 Lauramide, PEG-3 Cocamide, Cocamide DEA, and PPG-2 Hydroxyethyl Cocamide are significantly more mild to the eye than Cocamide MIPA and Cocamide MEA when present in the mild cleansing compositions of this invention.

I claim:

1. A personal cleansing composition comprising;
   a) a compound selected from the group consisting of polypropylene glycol-2 Hydroxyethyl Cocamide, polypropylene glycol-1 Hydroxyethyl Caprylamide, polypropylene glycol-3 Hydroxyethyl Linoleamide, and mixtures thereof; and
   b) at least one anionic surfactant;
   wherein the composition is mild.

2. The composition of claim 1 comprised of, based upon the total weight of the composition,
   from about 0.01% to about 10.0% of the compound; and
   from about 0.1% to about 20% of the anionic surfactant.

3. A personal cleansing composition comprising:
   a) a compound selected from the group consisting of polypropylene glycol-2 Hydroxyethyl Cocamide, polypropylene glycol-1 Hydroxethyl Caprylamide, polypropylene glycol-3 Hydroxyethyl Linoleamide, and mixtures thereof; and
   b) at least one anionic surfactant, wherein the anionic surfactant is selected from the group consisting of alkyt sulfates, alkyl ether sulfates, sulfosuccinates, isethionates, acyl amides, alkyl ether carboxylates, alkyl phosphates, and mixtures thereof, and wherein the composition is mild.

4. The composition of claim 1, further comprising at least one secondary surfactant selected from the group consisting of nonionic, amphoteric, betaine, cationic, and mixtures thereof.

5. The composition of claim 5, wherein the nonionic surfactant is selected from the group consisting of fatty alcohol acid ethoxylates, fatty alcohol amide ethoxylates, monoglyceride ethoxylates, sorbiten ester ethoxylates, alkyl polyglycosides, and mixtures thereof, and is present in an amount, based upon the total weight of the composition, from about 0.1% to about 30%.

6. The composition of claim 4, wherein the amphoteric surfactant is selected from the group consisting of alkylimino-diprorionates, alkylamphoglycinates (mono or di), alkylamphoproprionates (mono or di), alkylamphoacetates (mono or di), N-alkyl β-aminoproprionic acids, alkylpolyamino carboxylates, phosphorylated imidazolines, and mixtures thereof, and is present in an amount, based upon the total weight of the composition, from about 0.1% to about 20%.

7. The composition of claim 4, wherein the betaine surfactant is selected from the group consisting of alkyl betaines, alkylamido betaines, alkyl sultaines, alkylamido sultaines, and mixtures thereof and is present in an amount, based upon the total weight of the composition, from about 0.1% to about 15%.

8. The composition of claim 4, wherein the cationic surfactant is selected from the group consisting of alkyl quaternaries (mono, di, or tri), benzyl quaternaries, ester quaternaries, ethoxylated quaternaries, alkyl amines, and mixtures thereof and is present in the composition in an amount, based upon the total weight of the composition, from about 0.01% to about 20%.

9. The composition of claim 4, comprising, based upon the total weight of the composition
   a) from about 0.01% to about 10.0% of the compound;
   b) from about 0.1% to about 20% of at least one anionic surfactant selected frn the group consisting of alkyl sulfates, alkyl ether sulfates, sulfosuccinates, isethionates, acyl amides, alkyl ether carboxylates, alkyl phosphates, and mixtures thereof;
   c) from about 0.1% to about 30% of at least one nonionic surfactant selected from the group consisting of fatty alcohol acid ethoxytates, fatty alcohol amide ethoxylates, monoglyceride ethoxylates, sorbitan ester ethoxylates, alkyl polyglycosides, and mixtures thereof; and
   d) from about 0.1% to about 20% of at least one amphoteric surfactant selected from the group consisting of alkylamino-diproprionates, alkylamphoglycinates (mono or di), alkylamphoproprionates (mono or di), alkylamphoacetates (mono or di), N-alkyl β-aminoproprionic acids, alkylpolyamino carboxylates, phosphorylated imidazolines, and mixtures thereof.

10. The composition of claim 9 comprised of, based upon the total weight of the composition,
    from about 0.1% to about 7.0% of the compound:
    from about 0.5% to about 10% of anionic surfactant;
    from about 0.1% to about 20% of nonionic surfactant: and
    from about 0.1% to about 15% of amphoteric surfactant.

11. The composition of claim 9, further comprising, based upon the total weight of the composition,
    from about 0.1% to about 15% of at least one betaine selected from the group consisting of alkyl betaines, alkylamido betaines, alkyl sultaines, alkylamido sultaines, and mixtures thereof.

12. The composition of claim 11, wherein the composition is comprised of, based upon the total weight of the composition,
    from about 0.1% to about 7.0% of the compound;
    from about 0.5% to about 10% of anionic surfactant,
    from about 0.1% to about 20% of nonionic surfactant;
    from about 0.1% to about 15% of amphoteric surfactant; and
    from about 0.1% to about 10% of betaine.

13. The composition of claim 9, further comprising, based upon the total weight of the composition, from about 0.1% to about 20% of at least one cationic surfactant selected from the group consisting of alkyl quaternaries (mono, di, or tri), benzyl quaternaries, ester quaternaries, ethoxylated quaternaries, alkyl amines, and mixtures thereof.

14. The composition of claim 13, wherein the composition is comprised of, based upon the total weight of the composition,
    from about 0.1% to about 7.0% of the compound;
    from about 0.5% to about 10% of anionic surfactant;
    from about 0.1% to about 20% of nonionic surfactant;
    from about 0.1% to about 15% of amphoteric surfactant;
    from about 0.1% to about 10% of betaine; and
    from about 0.05% to about 15% of cationic surfactant.

15. The composition of claim 14, wherein the composition is comprised of
    based upon the total weight of the composition,
    from about 0.5% to about 3.0% of the compound;
    from about 0.75% to about 5.0% of anionic surfactant;
    from about 0.1% to about 15% of nonionic surfactant;
    from about 0.1% to about 10% of amphoteric surfactant:
    from about 0.1% to about 8.0% of betaine; and
    from about 0.1% to about 10% of cationic surfactant.

16. The composition of claim 3, further comprising at least one secondary surfactant selected from the group consisting of nonionic, amphoteric, betaine, cationic, and mixtures thereof.

17. The composition of claim 16, wherein the nonionic surfactant is selected from the group consisting of fatty alcohol acid ethoxytates, fatty alcohol amide ethoxylates. monoglyceride ethoxylates, sorbitan ester ethoxylates, alkyl polyglycosides, and mixtures thereof, and is present in an amount based upon the total weight of the composition, from about 0.1% to about 30%.

18. The composition of claim 16, wherein the amphoteric surfactant is selected from the group consisting of alkylimino-diproprionates, alkylamphoglycinates (mono or di), alkylamphoproprionates (mono or di), alkylamphoacetates (mono or di), N-alkyl β-aminoproprionic acids, alkylpolyamino carboxylates, phosphorylated imidazolines, and mixtures thereof, and is present in an amount, based upon the total weight of the composition, from about 0.1% to about 20%.

19. The composition of claim 16, wherein the betaine surfactant is selected from the group consisting of alkyl betaines, alkylamido betaines, alkyl sultaines, alkylamido sultaines, and mixtures thereof and is present in an amount, based upon the total weight of the composition, from about 0.1% to about 1 5%.

20. The composition of claim 16, wherein the cationic surfactant is selected from the group consisting of alkyl quaternaries (mono, di, or tri) benzyl quaternaries, ester quaternaries, ethoxylated quaternaries, alkyl amines, and mixtures thereof and is present in the composition in an amount, based upon the total weight of the composition, from about 0.01% to about 20%.

21. The composition of claim 16, comprising, based upon the total weight of the composition
 a) from about 0.01% to about 10.0% of the compound;
 b) from about 0.1% to about 30% of at least one nonionic surfactant selected from the group consisting of fatty alcohol add ethoxylates, fatty alcohol amide ethoxylates, monoglyceride ethoxylates, sorbitan ester ethoxylates, alkyl polyglycosides, and mixtures thereof; and
 c) from about 0.1% to about 20% of an amphoteric surfactant selected from the group consisting of alkylimino-diproprionates, alkylamphoglycinates (mono or di), alkylamphoproprionates (mono or di), alkylamphoacetates (mono or di), N-alkyl β-aminoproprionic acids, alkylpolyamino carboxylates, phosphorylated imidazolines, and mixtures thereof.

22. The composition of claim 21 comprised of, based upon the total weight of the composition,
 from about 0.1% to about 7.0% of the compound;
 from about 0.1% to about 20% of nonionic surfactant; and
 from about 0.1% to about 15% of amphoteric surfactant.

23. The composition of claim 21, wherein the composition is comprised of, based upon the total weight of the composition,
 from about 0.1% to about 7.0% of the compound;
 from about 0.1% to about 20% of nonionic surfactant;
 from about 0.1% to about 15% of amphoteric surfactant; and
 from about 0 1% to about 10% of betaine.

* * * * *